United States Patent [19]

Kulprathipanja et al.

[11] 4,319,058
[45] Mar. 9, 1982

[54] PROCESS FOR THE SEPARATION OF ETHANOL FROM WATER

[75] Inventors: Santi Kulprathipanja, Hoffman Estates; Richard W. Neuzil, Downers Grove, both of Ill.

[73] Assignee: UOP Inc., Des Plaines, Ill.

[21] Appl. No.: 195,917

[22] Filed: Oct. 10, 1980

[51] Int. Cl.$^3$ .............................................. C07C 29/76
[52] U.S. Cl. ...................... 568/917; 44/56; 528/396; 568/916
[58] Field of Search ................. 568/917, 916; 528/396

[56] References Cited

U.S. PATENT DOCUMENTS

| | | |
|---|---|---|
| 2,474,170 | 6/1949 | Sulzbacher . |
| 2,673,793 | 3/1954 | Brodhacker .......................... 44/53 |
| 2,712,532 | 7/1955 | Szwarc et al. ...................... 528/396 |
| 2,974,178 | 3/1961 | Hwa et al. .......................... 568/917 |
| 3,480,568 | 11/1969 | Weichman et al. .................. 528/396 |
| 3,753,773 | 8/1973 | Lee ..................................... 528/396 |
| 3,965,036 | 6/1976 | Himmelstein . |

Primary Examiner—Joseph E. Evans
Attorney, Agent, or Firm—James R. Hoatson, Jr.; Raymond H. Nelson; William H. Page, II

[57] ABSTRACT

Ethanol may be separated from a feed mixture comprising ethanol and water by contacting said feed mixture with an adsorbent comprising a shaped replication of particle aggregates comprising carbonaceous pyropolymers containing recurring units of at least carbon and hydrogen atoms at a temperature in the range of from about 20° to about 230° C. and a pressure in the range of from about atmospheric to about 500 psig, selectively adsorbing substantially all of the ethanol to the substantial exclusion of water and thereafter recovering high purity ethanol by passing a desorbing material over the adsorbent.

13 Claims, 4 Drawing Figures

PROCESS FOR THE SEPARATION OF ETHANOL FROM WATER

BACKGROUND OF THE INVENTION

Diminishing world supplies and availability of crude oil as well as sporadic regional shortfalls of gasoline for motor fuel have created considerable incentive for the development and use of alternative fuels. Ethanol is gaining wide popularity as such a fuel, particularly when mixed with gasoline to form a mixture known as gasohol. Gasohol may contain up to about 10 volume percent ethanol without modifications to presently used automobile engines being required, thereby extending the volume of motor fuel availability by a like percentage.

The primary source of the ethanol used in gasohol is derived primarily from the fermentation of mash, usually from corn. Natural fermentation is able to produce an ethanol-water product mixture containing at the most about 12 vol. % ethanol. It is therefore necessary to concentrate the ethanol by distillation which, of course, requires a great amount of energy, and, in fact, the greatest cost in production of ethanol by fermentation is the energy required to separate the ethanol from the water by distillation. A means of achieving this separation without such a great expenditure of energy would thus be extremely valuable. One, therefore, might consider the many known adsorptive separation processes known in the art for possible application to the separation of ethanol from water.

For example, it is well-known in the separation art that certain crystalline aluminosilicates can be used to separate hydrocarbon species from mixtures thereof. The separation of normal paraffins from branched chain paraffins, for example, can be accomplished by using a type A zeolite which has pore openings from 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules.

U.S. Pat. Nos. 3,265,750 and 3,510,423, for example, disclose processes in which large pore diameter zeolites such as the type X or type Y structured zeolites can be used to separate olefinic hydrocarbons.

In addition to separating hydrocarbon types, the type X or type Y zeolites have also been employed in processes to separate individual hydrocarbon isomers. In the process described in U.S. Pat. No. 3,114,782, for example, a particular zeolite is used as an adsorbent to separate alkyl-trisubstituted benzene; and in U.S. Pat. No. 3,668,267 a particular zeolite is used to separate specific alkyl-substituted naphthalenes. In processes described in U.S. Pat. Nos. 3,558,732, 3,686,342, and 3,997,620, adsorbents comprising particular zeolites are used to separate para-xylene from feed mixtures comprising para-xylene and at least one other xylene isomer by selectively adsorbing para-xylene over the other xylene isomers. In the last mentioned processes, the adsorbents used are para-xylene selective; para-xylene is selectively adsorbed and recovered as an extract component while the rest of the xylenes and ethylbenzenes are all relatively unadsorbed with respect to para-xylene and are recovered as raffinate components. Also, in the last mentioned processes, the adsorption and desorption may be continuously carried out in a simulated moving bed countercurrent flow system, the operating principles and sequence of which are described in U.S. Pat. No. 2,985,589.

Unfortunately, with the adsorbents of the above processes separation of ethanol from water would be out of the question because all of those adsorbents are hydrophilic, i.e. they would be selective for water over the ethanol. Thus, in using any of these adsorbents it would be necessary to extract the water which is the major component and reject the ethanol into the raffinate. Also, there would be the problem of what could be used as an effective desorbent. The separation of the desorbent, if possible, from the ethanol raffinate and water extract would be considerably more costly than the primary distillation of the alcohol from the water.

As hereinafter set forth in greater detail, it has now been discovered that certain compositions of matter have been found to be useful as a selective adsorbent for ethanol over water.

DETAILED DESCRIPTION OF THE INVENTION

This invention relates to a process for separating ethanol from water. More specifically, the invention is concerned with a process for separating and recovering ethanol from water utilizing, as a selective adsorbent for the ethanol, a shaped replication of a carbonaceous pyropolymer.

In one aspect an embodiment of this invention resides in a process for separating ethanol from a feed mixture comprising ethanol and water, which process comprises contacting at adsorption conditions said mixture with an adsorbent comprising a carbonaceous material, selectively adsorbing said ethanol to the substantial exclusion of water.

Another embodiment of this invention resides in a process for separating ethanol from a feed mixture comprising ethanol and water which process comprises contacting at adsorption conditions said mixture with an adsorbent comprising a carbonaceous material which process comprises the steps of maintaining net fluid flow through a column of said adsorbent in a single direction, which column contains at least three zones having separate operational functions occurring therein and being serially interconnected with the terminal zones of said column connected to provide a continuous connection of said zones, maintaining an adsorption zone in said column, said zone defined by the adsorbent located between a feed inlet stream at an upstream boundary of said zone and a raffinate outlet stream at a downstream boundary of said zone, maintaining a purification zone immediately upstream from said adsorption zone, said purification zone defined by the adsorbent located between an extract outlet stream at an upstream boundary of said purification zone and said feed inlet stream at a downstream boundary of said purification zone, maintaining a desorption zone immediately upstream from said purification zone, said desorption zone defined by the adsorbent located between a desorbent inlet stream at an upstream boundary of said zone and said extract outlet stream at a downstream boundary of said zone, passing said feed stream into said adsorption zone at adsorption conditions to effect the selective adsorption of said ethanol by said adsorbent in said adsorption zone and withdrawing a raffinate outlet stream from said adsorption zone, passing a desorbent material into said desorption zone at desorption conditions to effect the displacement of said ethanol from the adsorbent in said desorption zone, withdrawing an extract stream comprising said ethanol and desorbent material from said desorption zone, and periodically advancing through said column of adsorbent in a downstream direction with respect to fluid flow in said adsorption zone the feed inlet stream, raffinate outlet stream, desorbent inlet stream, and extract outlet stream to effect the shifting of zones through said adsorbent and the production of extract outlet and raffinate outlet streams.

A specific embodiment of this invention is found in a process for separating ethanol from a feed mixture comprising ethanol and water which comprises contacting said mixture with an adsorbent comprising a shaped replication of particle aggregates consisting of a carbonaceous pyropolymer containing at least carbon and hydrogen atoms at a temperature in the range of from about 20° to about 230° C. and a pressure in the range of from about atmospheric to about 500 psig, thereafter treating said adsorbent containing said ethanol with a desorbent material comprising toluene at a temperature in the range of from about 20° to about 230° C. and a pressure in the range of from about atmospheric to about 500 psig, and recovering the desired ethanol.

Other objects and embodiments will be found in the following further detailed description of the invention.

The adsorbents which are utilized in the processes of this invention to selectively adsorb ethanol to the substantial exclusion of water will comprise shaped replications of particle aggregates containing recurring units of at least carbon and hydrogen atoms. The shaped replications are prepared by treating an inorganic support of the desired shape such as spheres, plates, pellets, rods, fibers, monoliths, etc., with a pyropolymer precursor and thereafter pyropolymerizing said precursor by treatment at an elevated temperature which may range from about 400° to about 1200° C. to form at least a monolayer of a carbonaceous pyropolymer possessing recurring units containing at least carbon and hydrogen atoms on the surface of said inorganic support. The carbonaceous pyropolymer will adopt the shape of the inorganic support and thus be a replication of the starting inorganic support material. In the preferred embodiment of the present invention the inorganic support material will be characterized as having a surface area of from 1 to about 500 m$^2$/g; illustrative examples of refractory oxides which may be employed include alumina in various forms such as gamma-alumina, eta-alumina, theta-alumina, or mixtures of inorganic refractory oxides such as zeolites, silica-alumina, silica-zirconia, zirconia-titania, zirconia-alumina, etc.

In one method of preparing the composite, the inorganic support such as a refractory oxide is heated to a temperature of from about 400° to about 1200° C. in a reducing atmosphere containing an organic pyrolyzable compound. The organic pyropolymer precursors most commonly and preferably used for the purposes of this invention are members of the group consisting of aliphatic hydrocarbons, aliphatic halogen derivatives, aliphatic oxygen derivatives, aliphatic sulfur derivatives, aliphatic nitrogen derivatives, organometallic compounds, alicyclic compounds, aromatic compounds, and heterocyclic compounds. Of the aliphatic hydrocarbons, the more common classes which may be utilized to perform this invention are alkanes, alkenes, alkynes, and alkadienes. Ethane, propane, butane and pentane are among the alkanes which may be successfully used in the performance of this invention. Similarly, alkenes which suffice include ethene, propene, 1-butene, 2-butene and 1 pentene. Alkynes which may be successfully used include ethyne, propyne, 1-butyne, 2-butyne, 1-pentyne, and 1-hexyne, while 1,3-butadiene and isoprene are included among the alkadienes which may be utilized. Among the aliphatic halogen derivatives which suffice for the purposes of this invention are monohaloalkanes, polyhaloalkanes, and unsaturated halo compounds. In the monohaloalkane subgroup, chloromethane, bromethane, 1-iodopropane, and 1-chlorobutane may be used. Polyhaloalkanes such as carbn tetrachloride, chloroform, 1,2-dichloroethane and 1,2-dichlorobutane may also be utilized. One unsaturated halo compound which may be utilized is chloroprene.

The aliphatic oxygen derivatives appropriate for use in this invention include the classes of alcohols, ethers, halohydrides and alkene oxides, saturated aldehydes and ketones, unsaturated aldehydes and ketones, ketenes, acids, esters, salts and carbohydrates. Various alcohols which may be utilized include ethanol, 2-butanol, 1-propanol, glycol, (e.g. 1,3-propanediol), and glycerol. Ethers utilized include ethyl ether and isopropyl ether. Appropriate halohydrins and alkene oxides include ethylene chlorohydrin, propylene chlorohydrin, ethylene oxide, and propylene oxide. Suitable saturated aldehydes and ketones include formaldehyde, acetaldehyde, acetone, and ethyl methyl ketone. Unsaturated aldehydes and ketones which may be used include propenol, trans-2-butenal, and butenone. Ketene has also been successfully used as an organic pyrolyzable substance. Likewise, formic acid, acetic acid, oxalic acid, acrylic acid, chloroethanoic acid, formic anhydride and formyl chloride may also be utilized. Ethers such as methyl formate, ethyl formate and ethyl acetate may also be used. Salts such as sodium formate, potassium acetate and calcium propionate may be utilized as may a variety of carbohydrates. The broad classification of aliphatic sulfur derivatives may be broken down into the subclasses of alkanethiols, alkylthioalkanes, sulfonic acids, and alkyl sulfates and alkyl metallic sulfates. Suitable among the alkanethiols are ethyl mercaptan and n-propyl mercaptan. Among the alkylthioalkanes usable are the thio-ethers, alkyl sulfides, methyl sulfide, ethyl sulfide and methyl propyl sulfide. Ethyl sulfonic acid and n-propyl sulfonic acid are sulfonic acids which may also be successfully used. Ethyl sulfate and sodium laurel sulfate are also appropriate for use.

The broad class of aliphatic nitrogen derivatives may be broken down into the subclasses of nitroalkanes, amides, amines, nitriles and carbylamines. Nitroethane and 1-nitropropane are exemplary of suitable nitroalkanes while acetamide and propioamide are among the appropriate amides. Amines such as dimethylamine and ethylmethylamine, nitriles such as acetonitrile and propionitrile, and carbylamines such as ethyl isocyanide may also be used for the organic pyrolyzable substance of this invention. Organometallic compounds such as tetraisopropyl titanate, tetrabutyl titanate and 2-ethylhexyl titanate may also be used.

Particularly appropriate and preferred for use as the organic pyrolyzable substance of this invention are the alicyclic compounds. Foremost among these are cyclohexane and cyclohexene. Aromatic compounds include the subclasses of hydrocarbons, halogen compounds, oxygen derivatives, ethers, aldehydes, ketones, quinones, aromatic acids, aromatic sulfur derivatives; and aromatic nitrogen compounds may also be utilized. Among the many suitable hydrocarbons, benzene, naphthalene, anthracene, and toluene were successfully utilized. Benzyl chloride and benzal chloride are appropriate halogen compounds while phenol, o-cresol, benzyl alcohol and hydroquinone are among the suitable derivatives. Ethers such as anisole and phenetole and aldehydes, ketones, and quinones, such as benzaldehyde, acetophenone, benzophenone, benzoquinone and anthraquinone may also be used. Aromatic acids, such as benzoic acid, phenylacetic acid, and hydrocinnamic acid may be utilized while the aromatic sulfur derivative of benzene sulfonic acid will also serve successfully. The aromatic nitrogen compounds of nitrobenzene, 1-nitronaphthalene, aminobenzene and 2-amine toluene may also be successfully used as the organic pyrolyzable substance of this invention. Among the heterocyclic compounds, five member ring compounds such as furan, proline, coumarone, thionaphthene, indole, indigo, and carbazole may be successfully utilzed. Six member ring compounds such as pyran, coumarin and acridine may also be utilized.

As can be seen, an extremely wide latitude can be exercised in the selection of the organic pyrolyzable substance, since virtually any organic material that can be vaporized, decomposed and polymerized on the refractory oxide by heating will suffice. The resultant carbonaceous pyropolymer will possess recurring units containing at least carbon and hydrogen atoms, however, depending upon the pyropolymer precursor which has been selected, the pyropolymer may also contain other atoms such as nitrogen, oxygen, sulfur, or metals such as phosphorus, etc.

In another embodiment the composite may be prepared by impregnating the refractory inorganic oxide with a solution of a carbohydrate material such as dextrose, sucrose, fructose, starch, etc., and thereafter drying the impregnated support. After drying, the impregnated support is then subjected to pyrolysis temperatures in the range hereinbefore set forth whereby a carbonaceous pyropolymer similar in nature to those hereinbefore described is formed in at least a monolayer on the surface of the refractory inorganic oxide support.

Following this, the inorganic support is then chemically leached from the carbonaceous pyropolymer. The leaching is effected by treating said composite with either an acid or a base thereby forming a high surface area carbonaceous pyropolymer support which is a shaped replication of the original inorganic support. The leaching of the base material of the type hereinbefore set forth may be effected over a wide range of temperatures, said range being from about ambient (20°–25° C.) up to about 250° C. or more for a period of time which may range from less than 1 up to about 72 hours or more. It is to be understood that the operating parameters of the leaching step will vary over a wide range and will be dependent upon a combination of time, temperature, strength of the leaching solution, etc. Examples of acids or bases which may be utilized to leach out the base material, that is, the inorganic support such as a refractory inorganic oxide, will include inorganic acids such as phosphoric acid, sulfuric acid, nitric acid, hydrochloric acid, etc., organic acids such as methyl sulfonic acid, ethyl sulfonic acid, propyl sulfonic acid, toluene sulfonic acid, etc., strong bases such as sodium hydroxide, potassium hydroxide, lithium hydroxide, rubidium hydroxide, cesium hydroxide, etc. It is to be understood that the aforementioned leaching materials are only representative of the class of compounds which may be used and that any chemical which is capable of removing the refractory inorganic oxide while retaining the high surface area of the carbonaceous pyropolymer may be used.

The adsorbents used in the process of this invention can be better understood by brief reference to certain adsorbent properties which are necessary to the successful operation of a selective adsorption process. It will be recognized that improvements in any of these adsorbent characteristics will result in an improved separation process. Among such characteristics are: adsorptive capacity for some volume of an extract component per volume of adsorbent, the selective adsorption of an extract component with respect to a raffinate component and the desorbent material, sufficiently fast rates of adsorption and desorption of the extract component to and from the adsorbent, and, in instances where the components of the feed mixture are very reactive, little or no catalytic activity for undesired reactions such as polymerization and isomerization.

Feed mixtures to be utilized in the process of this invention will comprise a mixture of ethanol and water. To separate ethanol from a feed mixture containing ethanol and water, the mixture is contacted with the adsorbent and the ethanol is more selectively adsorbed and retained by the adsorbent while the water is relatively unadsorbed and is removed from the interstitial void spaces between the particles of adsorbent and the surface of the adsorbent. The adsorbent containing the ethanol is referred to as a "rich" adsorbent—rich in ethanol.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. Thus, the raffinate stream will contain as a raffinate component the feed mixture component other than the selected component and the extract stream will contain the selected component as the extract component.

Although it is possible by the process of this invention to produce high purity (98% or greater) ethanol product at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed ethanol to the concentration of a less selectively adsorbed water will be highest in the extract stream, next highest in the feed mixture, and lowest in the raffinate stream. Likewise, the ratio of the less selectively adsorbed water to the more selectively adsorbed ethanol will be highest in the raffinate stream, next highest in the feed mixture, and the lowest in the extract stream.

The adsorbent can be contained in one or more chambers where through programmed flow into and out of the chambers separation of the ethanol is effected. The adsorbent will preferably be contacted with a desorbent material which is capable of displacing the adsorbed ethanol from the adsorbent. The resultant extract stream comprising the ethanol and desorbent material may be subjected to a separation step so as to obtain high purity ethanol, however, when the desorbent material is one ordinarily useful for gasoline blending, the ethanol-desorbent mixture could be used directly for that purpose without a need for the separation step. Alternatively, the ethanol could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbed bed systems and are therefore preferred for use in our separation process. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589 incorporated herein by reference. In such a system, it is the progressive movement of multiple liquid access points down an adsorbent chamber that simulates the upward movement of adsorbent contained in the chamber. Only four of the access lines are active at any one time, the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of the process, it is generally necessary that three separate operational zones be present in order for the process to take place, although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation.

The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 could be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that the raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically, rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and, in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

References can be made to U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan, on April 2, 1969, incorporated herein by reference, for further explanation of the simulated moving-bed countercurrent process flow scheme.

Adsorption and desorption conditions for adsorptive separation processes can generally be either in the liquid or vapor phase or both. Preferred adsorption conditions for the process of this invention will include temperatures within the range of from about 20° C. to about 230° C. and will include pressures in the range of from about atmospheric to about 500 psig. Pressures higher than about 500 psig do not appear to effect the selectivity to a measurable amount and additionally would increase the cost of the process. Desorption conditions for the process of the invention shall generally include the same range of temperatures and pressures as described for adsorption operations. The desorption of the selectively adsorbed ethanol could also be effected at subatmospheric pressures or elevated temperatures or both or by vacuum purging of the adsorbent to remove the ethanol but this process is not directed to these desorption methods.

The desorbent materials which can be used in the various processing schemes employing this adsorbent will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

The desorbent material relied upon must be judiciously selected to satisfy several criteria. First, the desorbent material must displace the adsorbed ethanol from the adsorbent with reasonable mass flow rates without itself being so strongly adsorbed as to unduly prevent the ethanol from displacing the desorbent material in a following adsorption cycle. Secondly, desorbent materials must be compatible with the particular adsorbent and the particular feed mixture. More specifically, they must not reduce or destroy the critical selectivity of the adsorbent for the ethanol with respect to water.

Desorbent materials to be used in the process of this invention should additionally be substances which are either easily separable from the feed mixture that is passed into the process, or which are themselves useful for motor fuel blending when that is the desired use for the ethanol. In desorbing the preferentially adsorbed component of the feed, both desorbent material and the extract component are removed in admixture from the adsorbent. Without a method of separation such as distillation of these two materials, the purity of the extract component of the feed stock would not be very high since it would be diluted with desorbent. It is therefore contemplated, when pure ethanol is desired, that any desorbent material used in this process will have a substantially different average boiling point than that of the ethanol-water feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture. Preferred desorbent material for use in the process of this invention may be one or a mixture of the compounds toluene, methanol, pentane or benzene.

A dynamic testing apparatus may be employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect qualitatively or determine quantitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a non-adsorbed tracer and of an ethanol-water mixture, all diluted in desorbent, is injected for a duration of several minutes. Desorbent flow is resumed, and the tracer and the feed components are eluted as in a liquid-solid chromatographic operation. The effluent is collected in fractions and analyzed using chromatographic equipment and traces of the envelopes of corresponding component peaks developed.

From information derived from the test, adsorbent performance can be rated in terms of retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component of some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width, the faster the desorption rate.

Selectivity, (B), with regard to two given components, is equal to the quotient obtained by dividing the respective retention volumes of such components. Where selectivity of two components approaches 1.0, there is no preferential adsorption of one component by the adsorbent with respect to the other; they are both adsorbed (or non-adsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1.0, it is preferred that such selectivity be greater than 2.0. Like relative volatility, the higher the selectivity the easier the separation is to perform. Higher selectivities permit a smaller amount of adsorbent to be used. The rate of exchange relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exhange, less desorbent material has to be pumped through the process and separated from the extract stream for reuse in the process.

It is also necessary that the adsorbent possess little or no catalytic activity toward any reaction such as polymerization or isomerization of any of the feed components. Such activity might effect adsorbent capacity or selectivity or product yields, or all of these, but in the adsorptive separation of ethanol from water with a carbonaceous material adsorbent, this is generally not a problem.

To further evaluate promising adsorbent systems and to translate this type of data into a practical separation process, actual testing of the best system in a continuous countercurrent liquid-solid contacting device would be ideal. The general operating principles of such a device have been previously described and are found in U.S. Pat. No. 2,985,589 and a specific laboratory-size apparatus utilizing these principles is described in U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are withdrawn through two more. All remaining access lines are inactive and when the position of the distributing valve is advanced by one index, all active positions will be advanced by one bed. This simulates a condition in which the adsorbent physically moves in a direction countercurrent to the liquid flow. Additional details on adsorbent testing and evaluation may be found in the paper "Separation of $C_8$ Aromatics by Adsorption" by A. J. deRosset, R. W. Neuzil, A. J. Korous, and D. H. Rosback presented at the American Chemical Society, Los Angeles, Calif. Mar. 28 to Apr. 2, 1971. All of the above references are incorporated herein by reference.

The following examples are given for purposes of illustrating the process of the present invention utilizing as an adsorbent for the separation of ethanol from water, shaped replications of particle aggregates comprising a carbonaceous pyropolymer containing recurring units of at least carbon and hydrogen atoms. The drawings represent graphs showing the separation of ethanol from the water. However, it is to be understood that these examples are merely illustrative of the process, and that the present invention is not necessarily limited thereto.

EXAMPLE I

This example illustrates the results obtained by a pulse test utilizing the apparatus hereinbefore described.

Figure 1:
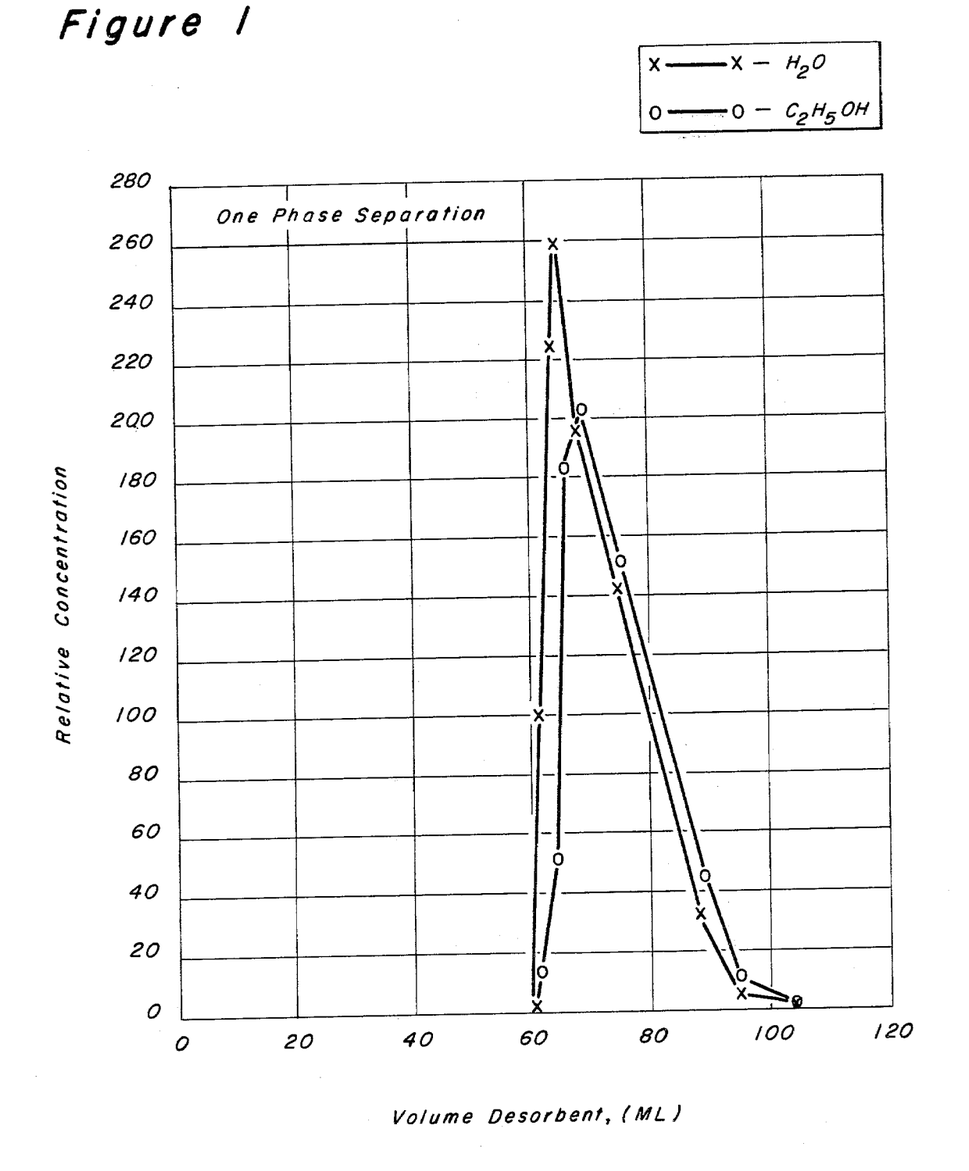

The adsorbent column was straight upflow with capillary controlled pressure. The feed pulses were 15 ml of a 50:50 mixture of ethanol and water. In this example the adsorbent chamber was packed with an adsorbent comprising a shaped replication of particle aggregates which had been prepared by treating alumina with benzene at a temperature of 800° C. and thereafter leaching the resulting component with phosphoric acid at a temperature of 160° C. for a period of 20 hours. The desorption material was methanol and the temperature of the column was maintained at 95° C. at a pressure sufficient to maintain liquid phase. FIG. 1 illustrates the results obtained by this test, said results clearly indicating that water was eluted first, followed by ethanol. This demonstrates that a clear separation of the ethanol and water was obtained.

EXAMPLE II

Figure 2:
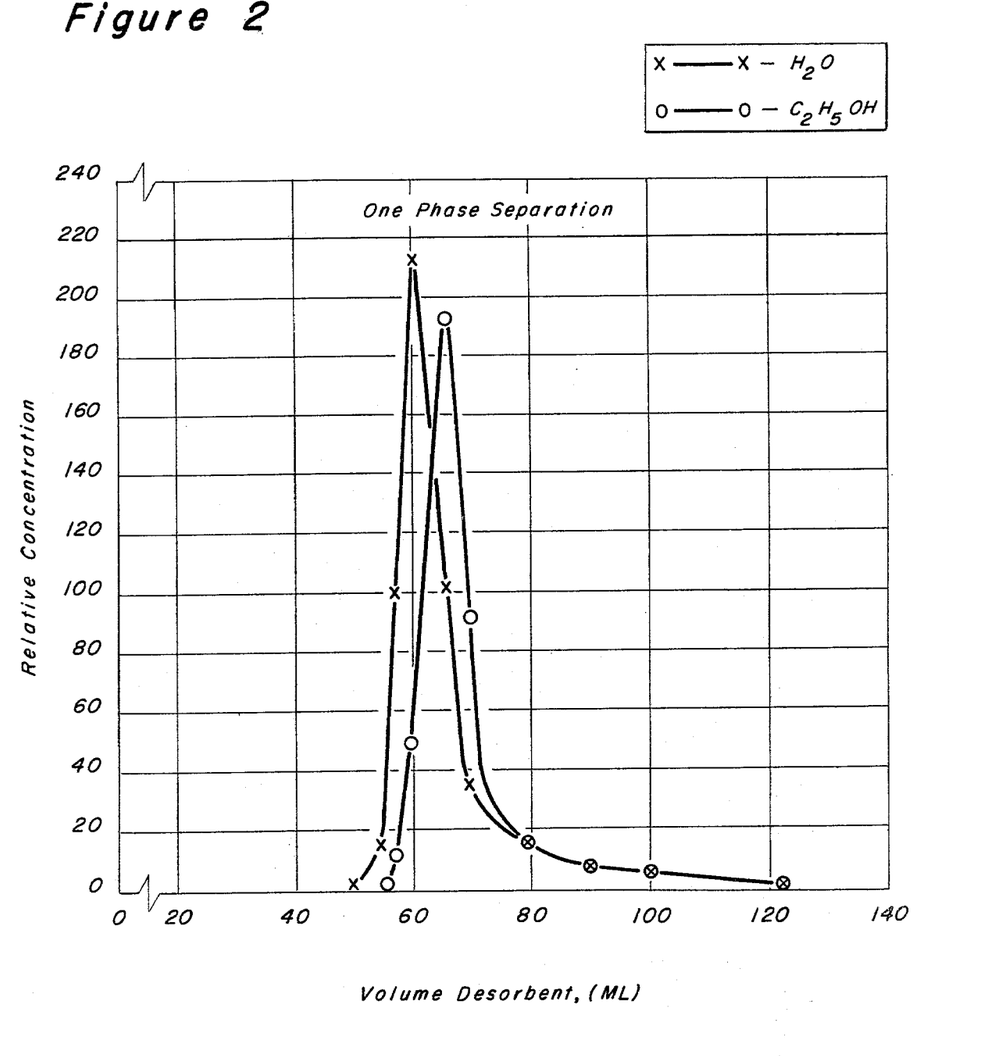

In the example, the column was packed with 13 grams of a shaped replication of particle aggregates prepared according to the method set forth in Example I above. Again, a feed comprising 15 ml of a 50:50 mixture of ethanol and water was pulsed over the adsorbent, followed by treatment with a desorbent comprising acetone. The feed was pulsed over the adsorbent in an upflow while maintaining a temperature of 95° C. at a pressure sufficient to maintain liquid phase. The results of this test are shown in FIG. 2 which demonstrates the elution first of water, followed by ethanol, thus clearly demonstrating a separation of the two components of the mixture.

EXAMPLE III

Figure 3:
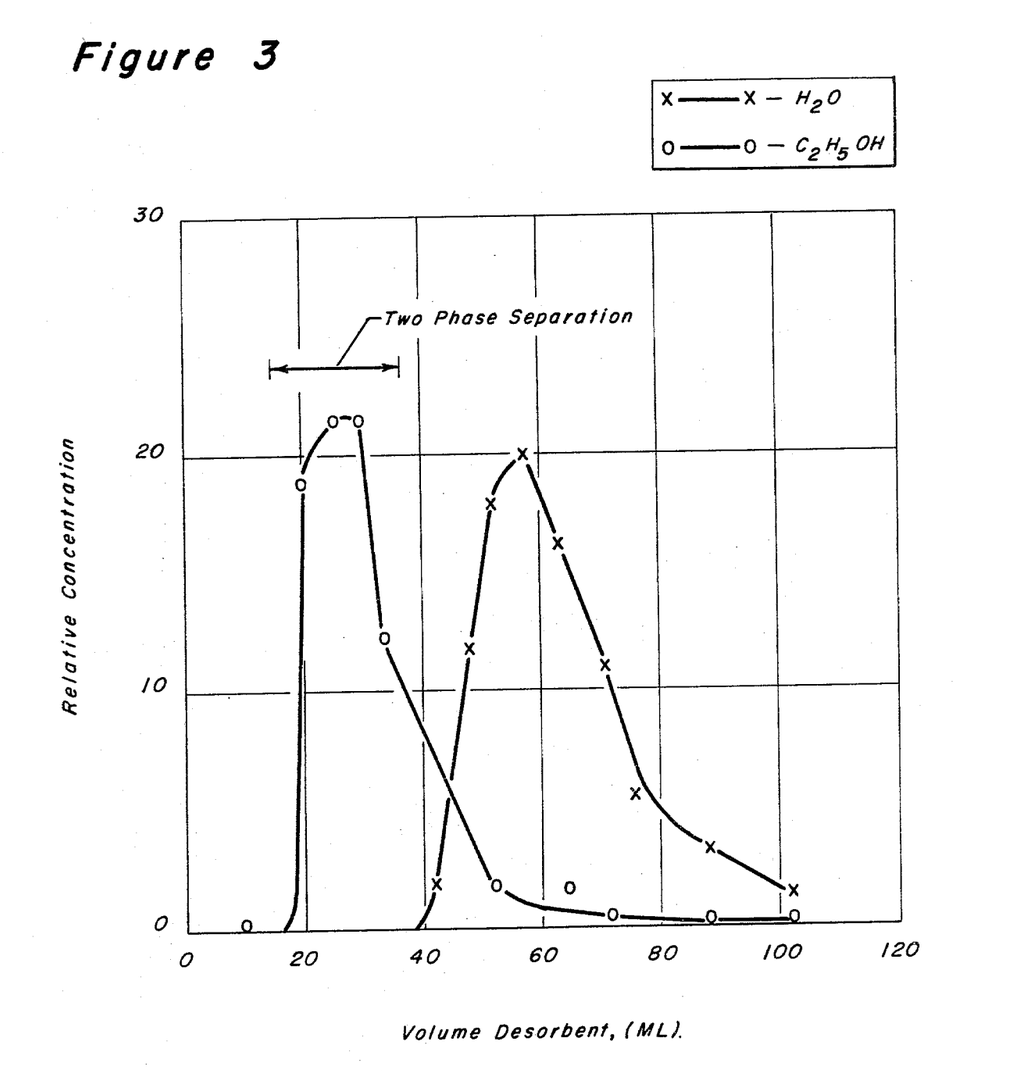

In this example, 13 grams of a shaped replication of particle aggregates prepared according to the method set forth in Example I above were packed in an adsorbent chamber and benzene was used as the desorbent material. A feed of 15 ml of a 50:50 ethanol:water mixture was passed over the material in a downflow direction while maintaining the temperature of the column at 95° C. and a pressure sufficient to maintain liquid phase. In this example, two phases exist during the time between effluent volumes of from 15 to 36 ml. The results of this separation are shown in FIG. 3 of the drawings which discloses a sharp separation between the ethanol and water.

EXAMPLE IV

Figure 4:
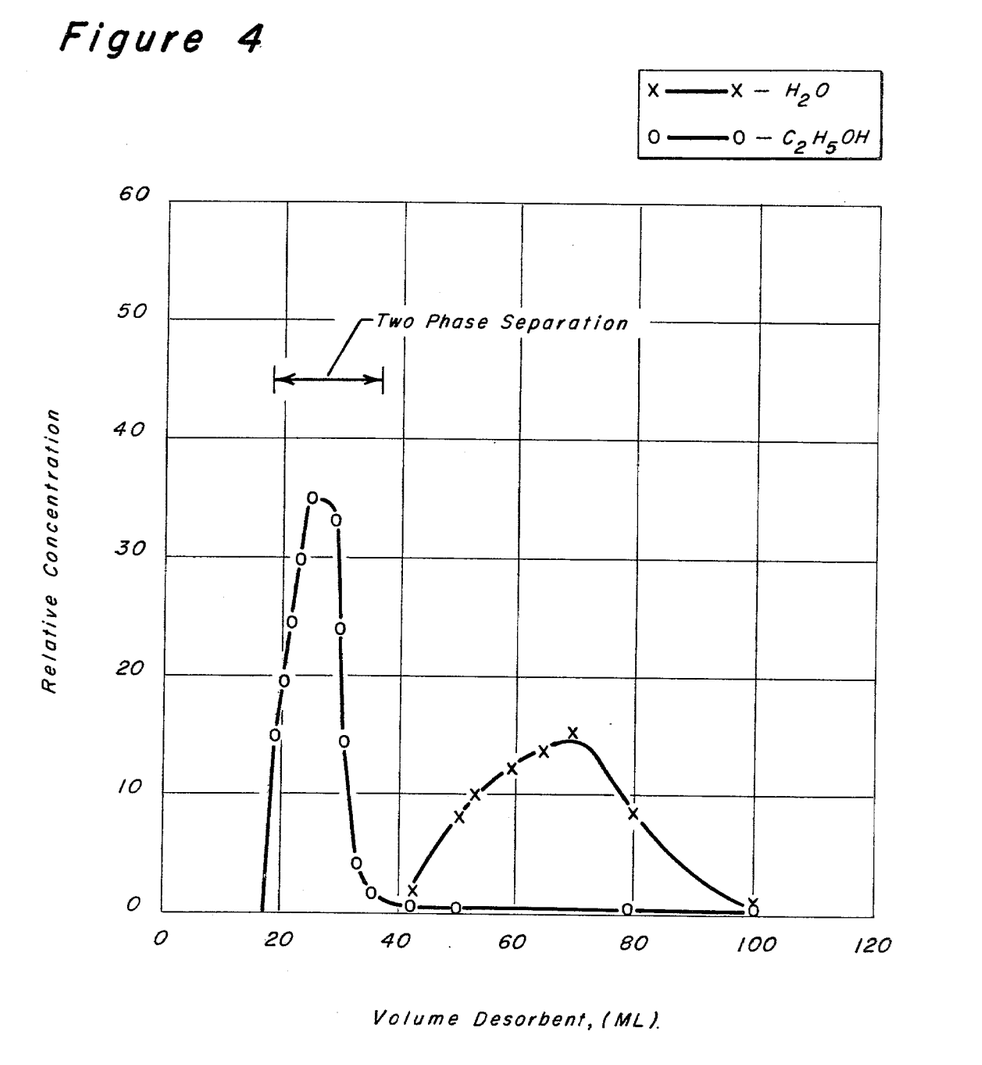

In this example, a separation between ethanol and water was effected by packing an adsorbent chamber with 13 grams of a shaped replication of particle aggregates similar in nature to that utilized in Example I above. The desorbent material which was utilized in this example comprised toluene. The temperature of the column was maintained at 95° C. and at a pressure sufficient to maintain liquid phase. The feed comprising a 50:50 mixture of ethanol and water was passed downflow through the column. However, in this example, two phases existed for the time from 19 to 36 ml. The results of the separation are shown in FIG. 4 of the drawing and illustrate a clear separation between the water and ethanol, but with an amount of water tailing.

We claim as our invention:

1. A process for separating ethanol from a feed mixture comprising ethanol and water which comprises contacting said mixture with an adsorbent consisting essentially of a shaped replication of particle aggregates prepared by treating an inorganic support with an organic pyropolymeric precursor, pyrolyzing said precursor at an elevated temperature ranging from about 400° C. to about 1200° C. to form a pyropolymer having at least a monolayer of recurring units containing at least carbon and hydrogen atoms on the surface of said inorganic support and thereafter leaching said inorganic support with an acid or base solution to form said pyropolymeric shape replicate, wherein said ethanol is adsorbed on said pyropolymeric shaped replicate to the selective exclusion of said water at adsorption conditions, and thereafter desorbing said ethanol from said pyropolymeric shaped replicate to obtain an ethanol-rich extract stream.

2. The process as set forth in claim 1 further characterized in that said adsorbent containing said ethanol is treated with a desorbent material to remove said ethanol therefrom as a fluid extract stream.

3. The process as set forth in claim 2 in which said desorbent material possesses an average boiling point substantially different from that of said feed mixture.

4. The process as set forth in claim 2 in which said desorbent material is selected from the group consisting of toluene, methanol, benezene and acetone.

5. The process of claim 4 further characterized in that high purity ethanol is recovered from said extract stream.

6. The process of claim 1 further characterized in that said adsorption conditions include a temperature in the range of from about 20° C. to about 230° C. and a pressure in the range of from about atmospheric to about 500 psig.

7. A process for separating ethanol from a feed mixture comprising ethanol and water which comprises contacting said mixture with an adsorbent consisting essentially of a shaped replication of particle aggregation prepared by treating an inorganic support with an organic pyropolymeric precursor, pyrolyzing said precursor at an elevated temperature ranging from about 400° C. to about 1200° C. to form a pyropolymer having at least a monolayer of recurring units containing at least carbon and hydrogen atoms on the surface of said inorganic support and thereafter leaching said inorganic support with an acid or base solution to form said pyropolymeric shaped replicate, wherein said separatory process comprises the steps of:

(a) maintaining a net fluid flow through a column of said shaped pyropolymeric replicate adsorbent in a single direction, which column contains at least three zones having separate operational functions occurring therein and being serially interconnected with the terminal zones of said column connecting to provide a continuous connection of said zones;

(b) maintaining an adsorption zone in said column, said zone being defined by the shaped pyropylymeric replicate adsorbent located between a feed inlet stream at an upstream boundary of said zone and a raffinate outlet stream at a downstream boundary of said zone;

(c) maintaining a purification zone immediately upstream from said adsorption zone, said purification zone being defined by the shaped pyropolymeric replicate adsorbent located between an extract outlet stream at an upstream boundary of said purification zone and said feed inlet stream at a downstream boundary of said purification zone;

(d) maintaining a desorption zone immediately upstream from said purification zone, said desorption zone being defined by the shaped pyropolymeric replicate adsorbent located between a desorbent inlet stream at an upstream boundary of said zone and said extract outlet stream at a downstream boundary of said zone;

(e) passing said feed stream into said adsorption zone at said adsorption conditions to effect the selective adsorption of said ethanol by said shaped pyropolymeric replicate adsorbent in said adsorption zone to the selective exclusion of water and withdrawing a water-rich raffinate outlet stream from said adsorption zone;

(f) passing a desorbent material into said desorption zone at desorption conditions to effect the displacement of said ethanol from said shaped pyropolymeric replicate adsorbent in said desorption zone;

(g) withdrawing an ethanol-rich extract stream comprising said ethanol and said desorbent material from said desorption zone;

(h) periodically advancing through said column of said shaped pyropolymeric replicate adsorbent in a downstream direction with respect to fluid flow in said adsorption zone the feed inlet stream, raffinate outlet stream, desorbent inlet stream, and extract outlet stream to effect the shifting of zones through said pyropolymeric adsorbent and the production of extract outlet and raffinate outlet streams.

8. The process as set forth in claim 7 further characterized in that said adsorption conditions and desorption conditions include a temperature in the range of about 20° to about 230° C. and a pressure in the range of from about atmospheric to about 500 psig.

9. The process of claim 8 further characterized in that said desorbent material possesses an average boiling point substantially different from that of said feed mixture.

10. The process of claim 9 further characterized in that said desorbent material is selected from the group consisting of toluene, methanol, benzene and acetone.

11. The process as set forth in claim 10 further characterized in that said high purity ethanol is recovered from said extract outlet stream.

12. The process of claim 7 further characterized in that it includes the step of maintaining a buffer zone immediately upstream from said desorption zone, said buffer zone being defined as the adsorbent located between the desorbent input stream at a downstream boundary of said buffer zone and a raffinate output stream at an upstream boundary of said buffer zone.

13. The process of claim 1 or 7 wherein said inorganic support and said organic pyropolymeric precursor are dried before said pyrolysis at said elevated temperatures ranging from about 400° C. to about 1200° C.

* * * * *